United States Patent
Mocadlo

(10) Patent No.: US 7,626,072 B2
(45) Date of Patent: Dec. 1, 2009

(54) ABSORBENT ARTICLES WITH A PATTERNED VISIBLE ACTIVE AGENT

(75) Inventor: Cheryl A. Mocadlo, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 109 days.

(21) Appl. No.: 10/328,338

(22) Filed: Dec. 23, 2002

(65) Prior Publication Data

US 2004/0122386 A1    Jun. 24, 2004

(51) Int. Cl.
*A61F 13/15*    (2006.01)
(52) U.S. Cl. .................. 604/359; 604/360; 604/385.01; 604/361
(58) Field of Classification Search ......... 604/359–361, 604/385.01; 428/207
See application file for complete search history.

(56) References Cited

U.S. PATENT DOCUMENTS

| | | | |
|---|---|---|---|
| 3,638,255 A * | 2/1972 | Sterrett ..................... | 5/641 |
| 4,623,340 A | 11/1986 | Luceri | |
| 4,684,956 A | 8/1987 | Ball | |
| 4,718,898 A | 1/1988 | Puletti et al. | |
| 4,758,276 A | 7/1988 | Lin et al. | |
| 4,762,520 A | 8/1988 | Wallstrom | |
| 4,778,458 A | 10/1988 | Gronostajski | |
| 5,019,062 A * | 5/1991 | Ryan et al. ................. | 604/359 |
| 5,122,407 A * | 6/1992 | Yeo et al. ................... | 428/138 |
| 5,154,960 A * | 10/1992 | Mucci et al. ................ | 428/68 |
| 5,161,686 A * | 11/1992 | Weber et al. ............... | 206/440 |
| 5,261,899 A * | 11/1993 | Visscher et al. ............ | 604/367 |
| 5,407,442 A * | 4/1995 | Karapasha .................. | 604/359 |
| 5,454,801 A | 10/1995 | Lauritzen | |
| 5,533,991 A | 7/1996 | Kirby et al. | |
| 5,582,603 A * | 12/1996 | Difilippantonio et al. ... | 604/380 |
| 5,613,962 A | 3/1997 | Kenmochi et al. | |
| 5,620,742 A | 4/1997 | Lauritzen | |
| 5,762,642 A | 6/1998 | Coles et al. | |
| 5,807,367 A | 9/1998 | Dilnik et al. | |
| 5,834,114 A | 11/1998 | Economy et al. | |
| 5,938,826 A | 8/1999 | Baker et al. | |
| 6,013,066 A | 1/2000 | Samuelsson | |
| 6,120,783 A | 9/2000 | Roe et al. | |

(Continued)

FOREIGN PATENT DOCUMENTS

DE    19603840    8/1997

(Continued)

OTHER PUBLICATIONS

U.S. Appl. No. 09/991,185, filed Nov. 16, 2001.

(Continued)

*Primary Examiner*—Jacqueline F. Stephens
(74) *Attorney, Agent, or Firm*—Dority & Manning, P.A.

(57) ABSTRACT

An absorbent article includes an odor control agent deposited in a visible pattern on a material layer of the article. The odor control agent has a color so as to present a distinguishable pattern against a contrasting colored background defined by the material layer. The article includes a top cover defining a bodyfacing surface of the absorbent article, and the odor control agent is disposed beneath the bodyfacing surface and is visible through the top cover, or may be deposited directly on the bodyfacing surface of the top cover.

16 Claims, 5 Drawing Sheets

U.S. PATENT DOCUMENTS

| | | |
|---|---|---|
| 6,140,551 A | 10/2000 | Niemeyer et al. |
| 6,149,934 A | 11/2000 | Krzysik et al. |
| 6,258,997 B1 | 7/2001 | Johansson et al. |
| 6,365,794 B1 | 4/2002 | Dabi et al. |
| 6,376,741 B1 | 4/2002 | Guarracino et al. |
| 6,395,957 B1 | 5/2002 | Chen et al. |
| 6,417,426 B1 | 7/2002 | Takai et al. |
| 6,440,111 B1 | 8/2002 | Berba et al. |
| 6,476,288 B1 | 11/2002 | VanRijswijck et al. |
| 2001/0024716 A1 | 9/2001 | Chen et al. |
| 2002/0068917 A1 | 6/2002 | VanGompel et al. |
| 2002/0077618 A1 | 6/2002 | Molas |
| 2002/0110689 A1 | 8/2002 | Hu et al. |
| 2002/0128615 A1 | 9/2002 | Tyrrell et al. |
| 2002/0138054 A1 | 9/2002 | Erdman et al. |
| 2005/0112085 A1 * | 5/2005 | MacDonald et al. ....... 424/76.1 |
| 2005/0131363 A1 * | 6/2005 | MacDonald et al. ........ 604/367 |

FOREIGN PATENT DOCUMENTS

| | | |
|---|---|---|
| DE | 19816393 | 10/1999 |
| EP | 0140560 | 11/1988 |
| EP | 0392528 | 10/1990 |
| EP | 0526225 | 2/1993 |
| EP | 592001 A1 * | 4/1994 |
| EP | 0604729 | 7/1994 |
| EP | 0748894 | 12/1996 |
| EP | 0698138 | 7/1999 |
| EP | 0951889 | 10/1999 |
| EP | 1099434 A1 | 5/2001 |
| EP | 0746296 | 6/2001 |
| EP | 1120097 | 8/2001 |
| EP | 1166732 | 1/2002 |
| GB | 807768 | 1/1959 |
| GB | 2284767 | 6/1995 |
| GB | 2308303 | 6/1997 |
| KR | 2001001489 A * | 1/2001 |
| WO | 9319715 | 10/1993 |
| WO | 9836722 | 8/1998 |
| WO | 9915123 | 4/1999 |
| WO | 0145757 | 6/2001 |
| WO | 0197972 | 12/2001 |
| WO | WO 0207661 A2 * | 1/2002 |
| WO | 03013406 | 2/2003 |
| WO | 03043554 | 5/2003 |

OTHER PUBLICATIONS

U.S. Appl. No. 09/990,686, filed Nov. 16, 2001.
U.S. Appl. No. 10/334,159, filed Dec. 30, 2002.
EPO Search Report Mar. 30, 2004.

* cited by examiner

ABSORBENT ARTICLES WITH A PATTERNED VISIBLE ACTIVE AGENT

FIELD OF THE INVENTION

The present invention relates generally to the field of absorbent articles, for example feminine care absorbent articles, and more particularly to an absorbent article incorporating an active agent.

BACKGROUND

Feminine care absorbent articles, such as sanitary napkins and pantiliners, typically include an absorbent structure enclosed between a body facing liquid permeable top cover and a liquid impermeable outer cover. The top cover and outer cover may extend laterally beyond the absorbent and be bonded together to form a peripheral seal around the article. The articles are positioned in the crotch portion of an undergarment for absorption of bodily exudates.

While the primary focus of absorbent articles remains the ability of the articles to absorb and retain fluids, additional functions, such as odor control (for perceived discretion and cleanliness benefits) are also receiving increased attention. A wide range of compounds that result in the production of malodors may be contained in absorbed fluids or their degradation products and thus be present within an absorbent article during use. Examples of these compounds include fatty acids, ammonia, amines, sulfur-containing compounds, ketones, and aldehydes.

The use of various odor controlling agents in absorbent articles in order to address the problem of malodour formation is well known in the art. These agents are typically classified according to the type of odor the agent is intended to combat. In general, odors may be classified as being acidic, basic, or neutral.

Carbon has been noted in the art as being particularly effective over a broad spectrum of odors. However, the use of carbon presents challenges to manufacturers of absorbent articles. For example, carbon is not generally favored due to its black appearance. Certain consumers find this unacceptable from an appearance standpoint. Also, the readily discernable presence of the carbon "announces" the fact that an odor control agent is necessary. This may be a source of embarrassment to consumers. In this regard, efforts have been made to bleach or whiten such agents, or to hide the agents within or between layers of the absorbent article. Efforts have also been made at incorporating various "light colored" odor control agents into absorbent articles. Reference is made for example to U.S. Pat. No. 6,376,741 B1, which describes the use of a combination of zeolite and silica as an odor control agent for use in absorbent articles.

The present invention relates to the use of highly visible odor control agents in absorbent articles in a non-offensive and aesthetically pleasing manner.

SUMMARY

Objects and advantages of the invention will be set forth in part in the following description, or may be obvious from the description, or may be learned through practice of the invention.

In accordance with certain aspects of the invention, an absorbent article is provided with an odor control agent in a pattern that presents a stark and highly visible contrast against a differently colored background. For example, the odor control agent may be a dark color applied against a light background. Alternatively, the odor control agent may be a light color applied against a dark background. The invention is premised on the concept of hiding or disguising the odor control agent "in plain sight." The odor control agent is applied to a component of the absorbent article in an aesthetically pleasing and highly visible pattern. Thus, instead of being hidden within the article, the odor control agent is used to change the overall appearance of the article much like paint applied to a canvas.

The invention is not limited to any particular type of absorbent article, and may have benefits for a wide variety of articles in differing fields. For example, articles in the healthcare field such as ostomy bags, surgical gowns and drapes, and wound dressings may benefit from aspects of the invention. The invention has particular usefulness for any manner of personal hygiene articles, such as diapers, training pants, feminine care articles, incontinence articles, and the like. Articles such as wristbands, sweatbands, shoe insoles, and so forth will also benefit from the invention. In general, the invention will have usefulness for any article that is used to absorb bodily fluids.

The agent may be applied to a top cover member of the article, or to an underlying material so long as the patterned agent is visible through the cover layer.

The particular type or style of pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. The pattern may be targeted for a specific class of consumers. For example, in the case of diapers or training pants, the pattern may be in the form of cartoon characters, or the like. It should be appreciated that the "pattern" may take on virtually any desired appearance. The pattern may encompass between about 10% to about 75% of the surface area of a top cover material of bodyfacing surface of the article.

In an embodiment wherein the article is a feminine care article, the pattern may be concentrated in a generally central "insult" area of the bodyfacing surface. In this embodiment, the agent may be dark colored and serve the additional function of masking or otherwise making stains less visible.

The odor control agent is "highly visible" in that it is easily discernable against its background. For example, the background material (i.e, the cover layer, underlying absorbent material, intake layer, etc.) may be white or light colored, and the odor control agent may be dark colored, or contained in a dark colored mixture, etc.

Although the invention is not limited to use of carbon as the odor control agent, activated carbon is desirable due to its black appearance and broad spectrum odor control capabilities. However, any known odor control agent may be used so long as it presents the desired contrast, or is contained in a mixture presenting the desired contrast. For example, a light colored agent such as zeolite or silica may be used if applied to the article with a dark colored binder or adhesive, or as a component of a dark colored mixture applied to the article. Alternatively, a light colored agent such as zeolite or silica may be applied against a dark colored background.

As a measure of the degree of visibility of the odor control agent (or contrast of the agent against a background), an image analysis method was developed to determine the gray-level difference between the odor control agent and the product background. The gray-level difference may be at least about 45 on a scale of 0-255, where 0 represents "black" and 255 represents "white."

A variety of techniques may be utilized to apply the odor control agent in the desired pattern. For example, a mixture containing particulate carbon particles may be formulated to specifically adhere or bind to a material of the absorbent article. The mixture may contain, for example, an adhesive, molten polymeric material, binder, etc., with the carbon particles suspended therein. The mixture may be applied in the desired pattern by any known method of application, such as print (including screen printing), spraying, contact coated, blade, saturant, coating, droplet throw, paint, and foam applications. In an alternate embodiment, an adhesive may be applied in a desired pattern onto a substrate with subsequent application of a particulate odor control agent. Similarly, a particulate agent may be applied in a desired pattern to an adhesive coated substrate.

In another embodiment, the odor control agent may be applied in the form of an activated carbon coating, such coating formed, for example, from a polymeric material and an activation agent. The coating may become activated by being heated to a temperature sufficient for the activation agent to react with the polymeric material to induce carbon activation. The polymeric material may be initially dissolved in a solvent, mixed with the chemical activation agent, and then applied to the absorbent article material by any known method of application, as discussed above. An inkjet printing technique may be beneficial for applying the mixture in the desired pattern.

Other features and aspects of the present invention are discussed in greater detail below by way of reference to particular embodiments.

DETAILED DESCRIPTION

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

As discussed above, the present invention relates to any manner of absorbent article, and has particular usefulness with personal hygiene articles such as diapers, training pants, swim pants, incontinence articles, feminine care articles, and the like. The construction and materials used in conventional absorbent articles vary widely and are well known to those of skill in the art. A detailed explanation of such materials and construction of conventional articles is not necessary for purposes of describing the present invention. The invention has particular usefulness for feminine care articles and, for purposes of illustration and description only, embodiments of feminine care articles according to the invention, in particular sanitary napkins, are referenced herein. However, it should be appreciated that the invention is in no way limited to sanitary napkins in particular, or to feminine care articles in general.

Figure 1:
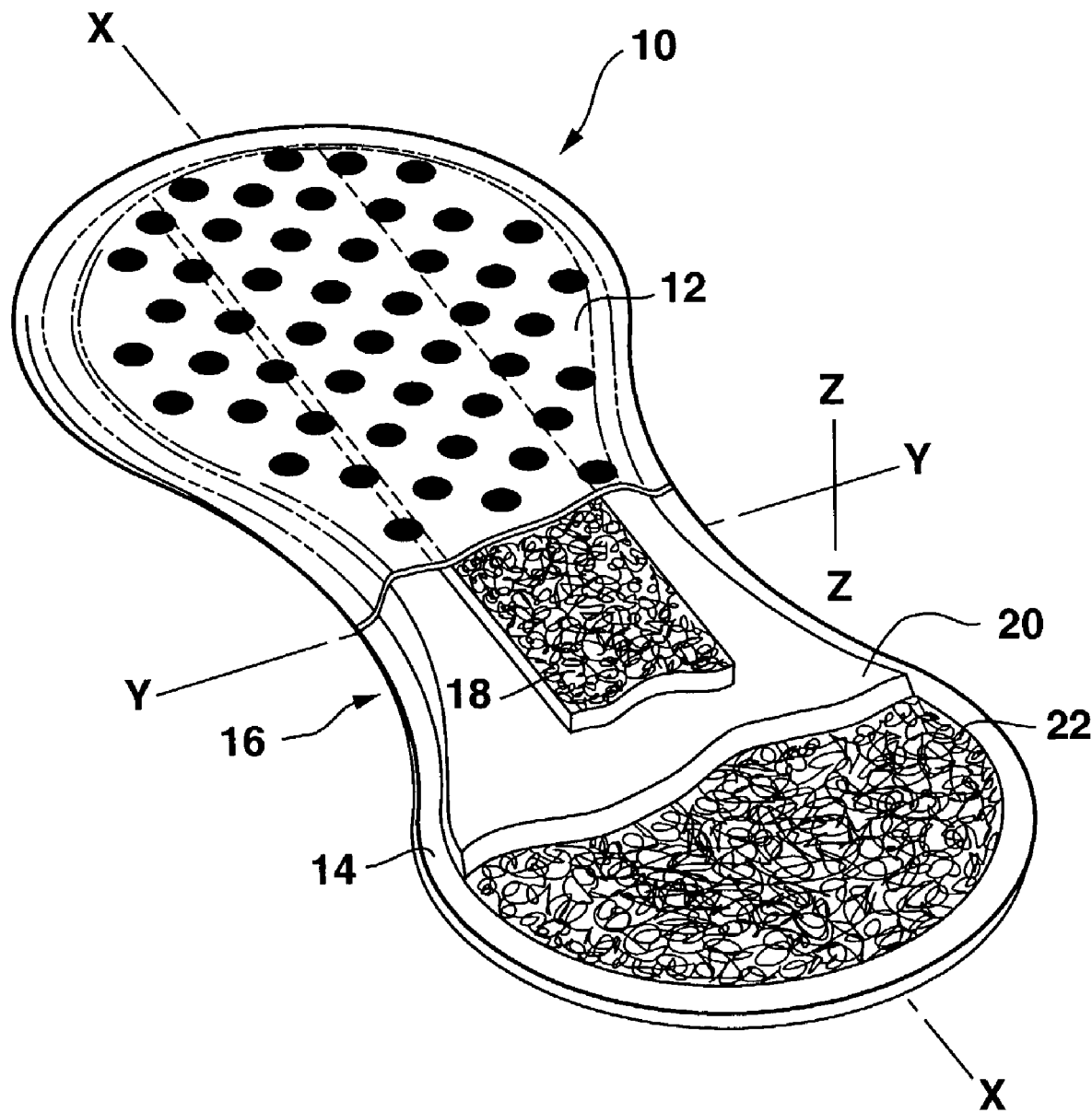
FIG. 1 is a perspective and partial cut-away of an exemplary absorbent article according to the invention.

In this regard, various embodiments of an absorbent article that may be formed according to the present invention will now be described in more detail. For purposes of illustration only, an absorbent article 10 is shown in FIG. 1 as a sanitary napkin for feminine hygiene. In the illustrated embodiment, the absorbent article 10 includes a top cover 12, an outer cover or baffle 14, and an absorbent core structure 16. The top cover 12 defines a bodyfacing surface of the article 10. The absorbent core 16 is positioned inward from the outer periphery of the absorbent article 10 and includes a body-facing side positioned adjacent the cover 12 and a garment-facing surface positioned adjacent the baffle 14.

The cover 12 is generally designed to contact the body of the user and is liquid-permeable. The cover 12 can surround the absorbent core 16 so that it completely encases the absorbent article 10. Alternatively, the cover 12 and the baffle 14 can extend beyond the absorbent core 16 and be peripherally joined together, either entirely or partially, using known techniques. Typically, the cover 12 and the baffle 14 are joined by adhesive bonding, ultrasonic bonding, or any other suitable joining method known in the art.

The liquid-permeable cover 12 is sanitary, clean in appearance, and somewhat opaque to hide bodily discharges collected in and absorbed by the absorbent core 16. The cover 12 further exhibits good strike-through and rewet characteristics permitting bodily discharges to rapidly penetrate through the cover 12 to the absorbent core 16, but not allow the body fluid to flow back through the cover 12 to the skin of the wearer. For example, some suitable materials that can be used for the cover 12 include nonwoven materials, perforated thermoplastic films, or combinations thereof. A nonwoven fabric made from polyester, polyethylene, polypropylene, bicomponent, nylon, rayon, or like fibers may be utilized. For instance, a white uniform spunbond material is particularly desirable because the color exhibits good masking properties to hide menses that has passed through it. U.S. Pat. No. 4,801,494 to Datta, et al. and U.S. Pat. No. 4,908,026 to Sukiennik. et al. teach various other cover materials that can be used in the present invention. If desired, the cover 12 may be incorporated with an activated carbon coating in accordance with the present invention to enable it to better function in reducing odors of bodily fluids.

The cover 12 can also contain a plurality of apertures (not shown) formed therethrough to permit body fluid to pass more readily into the absorbent core 16. The apertures can be randomly or uniformly arranged throughout the cover 12, or they can be located only in the narrow longitudinal band or strip arranged along the longitudinal axis X-X of the absorbent article 10. The apertures permit rapid penetration of body fluid down into the absorbent core 16. The size, shape, diameter and number of apertures can be varied to suit one's particular needs.

As stated above, the absorbent article also includes a baffle 14. The baffle 14 is generally liquid-impermeable and designed to face the inner surface, i.e., the crotch portion of an undergarment (not shown). The baffle 14 can permit a passage of air or vapor out of the absorbent article 10, while still blocking the passage of liquids. Any liquid-impermeable material can generally be utilized to form the baffle 14. For example, one suitable material that can be utilized is a micro-embossed polymeric film, such as polyethylene or polypropylene. In particular embodiments, a polyethylene film is utilized that has a thickness in the range of about 0.2 mils to about 5.0 mils, and particularly between about 0.5 to about 3.0 mils. If desired, the baffle 14 may be incorporated with an activated carbon coating in accordance with the present invention to enable it to better function in reducing odors of bodily fluids.

As indicated above, the absorbent article 10 also contains an absorbent core 16 positioned between the cover 12 and the baffle 14. In the illustrated embodiment, for example, the absorbent core 16 contains three separate and distinct absorbent members 18, 20 and 22. It should be understood, however, that any number of absorbent members can be utilized in the present invention. For example, in one embodiment, only the absorbent member 22 may be utilized in an effort to simplify the article 10 in terms of the number of necessary layers and registration between the layers. Such a simplified design can readily incorporate an odor control agent near the top (body facing) surface of the article.

As shown, the first absorbent member 18, or intake member, is positioned between the cover 12 and the second absorbent member 20, or transfer delay member.

Typically, the intake member 18 is made of a material that is capable of rapidly transferring, in the z-direction, body fluid that is delivered to the cover 12. Intake, not capacity, is the most important function for the intake member 18. Since the efficacy of some odor control agents is reduced in the presence of moisture, utilizing an intake member with minimal capacity is preferred for this invention. For executions incorporating an intake member with high capacity, utilization of an innately hydrophobic or a hydrophobically-coated odor control agent is preferred.

The intake member 18 can generally have any shape and/or size desired. For example, in one embodiment, the intake member 18 has a rectangular shape, with a length equal to or less than the overall length of the absorbent article 10, and a width less than the width of the absorbent article 10. For example, a length of between about 150 mm to about 300 mm and a width of between about 10 mm to about 60 mm can be utilized.

Because the intake member 18 is generally of a dimension narrower than the absorbent article 10, the sides of the intake member 18 are spaced away from the longitudinal sides of the absorbent article 10 and the body fluid is restricted to the area within the periphery of the intake member 18 before it passes down and is absorbed into the transfer delay member 20. This design enables the body fluid to be combined in the central area of the absorbent article 10 and to be wicked downward.

In general, any of a variety of different materials are capable of being used for the intake member 18 to accomplish the above-mentioned functions. The material may be synthetic, cellulosic, or a combination of synthetic and cellulosic materials. For example, airlaid cellulosic tissues may be suitable for use in the intake member 18. The airlaid cellulosic tissue can have a basis weight ranging from about 10 grams per square meter (gsm) to about 300 gsm, and in some embodiments, between about 100 gsm to about 250 gsm. In one embodiment, the airlaid cellulosic tissue has a basis weight of about 200 gsm. The airlaid tissue can be formed from hardwood and/or softwood fibers. The airlaid tissue has a fine pore structure and provides an excellent wicking capacity, especially for menses.

In certain embodiments, a second absorbent member 20, or transfer delay member, may be positioned vertically below the intake member 18. In a more simplified design, a transfer delay member may be omitted. In some embodiments, the transfer delay member 20 contains a material that is less hydrophilic than the other absorbent members, and may generally be characterized as being substantially hydrophobic. For example, the transfer delay member 20 may be a nonwoven fibrous web composed of a relatively hydrophobic material, such as polypropylene, polyethylene, polyester or the like, and also may be composed of a blend of such materials. One example of a material suitable for the transfer delay member 20 is a spunbond web composed of polypropylene, multi-lobal fibers. Further examples of suitable transfer delay member materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay member 20 are described in U.S. Pat. No. 4,798,603 to Meyer, et al. and U.S. Pat. No. 5,248,309 to Serbiak, et al., which are incorporated herein in their entirety by reference thereto for all purposes. To adjust the performance of the invention, the transfer delay member 20 may also be treated with a selected amount of surfactant to increase its initial wettability.

The transfer delay member 20 can generally have any size, such as a length of about 150 mm to about 300 mm. Typically, the length of the transfer delay member 20 is approximately equal to the length of the absorbent article 10. The transfer delay member 20 can also be equal in width to the intake member 18, but is typically wider. For example, the width of the transfer delay member 20 can be from between about 50 mm to about 75 mm, and particularly about 48 mm.

The transfer delay member 20 of the absorbent core 16 typically has a basis weight less than that of the other absorbent members. For example, the basis weight of the transfer delay member 20 is typically less than about 150 grams per square meter (gsm), and in some embodiments, between about 10 gsm to about 100 gsm. In one particular embodiment, the transfer delay member 20 is formed from a spunbonded web having a basis weight of about 30 gsm.

Besides the above-mentioned members, the absorbent core 16 also includes a composite member 22. For example, the composite member 22 can be a coform material. In this instance, fluids can be wicked from the transfer delay member 20 into the absorbent member 22. The composite absorbent member 22 may be formed separately from the intake member 18 and/or transfer delay member 20, or can be formed simultaneously therewith. In one embodiment, for example, the composite absorbent member 22 can be formed on the transfer delay member 20 or intake member 18, which acts a carrier during the coform process described above.

The absorbent article 10 may also contain other components as well. For instance, in some embodiments, the lower surface of the baffle 14 can contain an adhesive for securing the absorbent article 10 to an undergarment. In such instances, a backing (not shown) may be utilized to protect the adhesive side of the absorbent article 10 so that the adhesive remains clean prior to attachment to undergarment. The backing can generally have any desired shape or dimension. For instance, the backing can have a rectangular shape with dimension about 17 to about 24 cm in length and about 6.5 to 10.5 cm in width. The backing is designed to serve as a releasable peel strip to be removed by the user prior to attachment of the absorbent article 10 to the undergarment. The backing serving as a releasable peel strip can be a white Kraft paper that is coated on one side so that it can be released readily from the adhesive side of the absorbent article 10. The coating can be a silicone coating, such as a silicone polymer commercially available from Akrosil of Menasha, Wis.

Once formed, the absorbent article 10 generally functions to absorb and retain fluids, such as menses, blood, urine, and other excrements discharged by the body during a menstrual period. For example, the intake member 18 can allow the body fluid to be wicked downward in the z-direction and away from the cover 12 so that the cover 12 retains a dry and comfortable feel to the user. Moreover, the intake member 18 can also absorb a significant amount of the fluid. The composite absorbent member 22 then wicks the fluid along its length and width (-x and -y axis). Therefore, the composite absorbent member 22 can become completely saturated before the fluid is taken up by the transfer delay member 20. The fluid is also wicked along the length of the transfer delay member 20 and the composite absorbent member 22, thereby keeping the fluid away from the edges of the absorbent article 10. This allows for a greater utilization of the absorbent core 16 and helps reduce the likelihood of side leakage.

Although one embodiment of an absorbent article has been described above that may incorporate the benefits of the present invention, it should be understood that other absorbent article configurations are also included within the scope of the present invention. For instance, other absorbent configurations are described in U.S. Pat. No. 5,197,959 to Buell; U.S. Pat. No. 5,085,654 to Buell; U.S. Pat. No. 5,634,916 to Lavon, et al.; U.S. Pat. No. 5,569,234 to Buell, et al.; U.S. Pat. No. 5,716,349 to Taylor, et al.; U.S. Pat. No. 4,950,264 to Osborn; U.S. Pat. No. 5,009,653 to Osborn; U.S. Pat. No. 5,509,914 to Osborn; U.S. Pat. No. 5,649,916 to DiPalma, et al.; U.S. Pat. No. 5,267,992 to Van Tillburg; U.S. Pat. No. 4,687,478 to Van Tillburg; U.S. Pat. No. 4,285,343 to McNair; U.S. Pat. No. 4,608,047 to Mattingly; U.S. Pat. No. 5,342,342 to Kitaoka; U.S. Pat. No. 5,190,563 to Herron, et al.; U.S. Pat. No. 5,702,378 to Widlund, et al.; U.S. Pat. No. 5,308,346 to Sneller, et al.; U.S. Pat. No. 6,110,158 to Kielpikowski; and WO 99/00093 to Patterson, et al., which are incorporated herein in their entirety by reference thereto for all purposes.

In the FIGS. 2A through 7, the odor control agent 26 is depicted as a dark colored agent against a light colored background. It should be understood that this is for illustrative purposes only. The invention also encompasses a light colored agent against a dark colored background. Thus, it should be appreciated that the converse of the patterns (light pattern against dark background) illustrated in the figures are also within the scope and spirit of the invention.

It should be appreciated that various patterns will encompass varying degrees of the overall surface area of the bodyfacing surface of the article. In general, the pattern may encompass between about 10% to about 75% of the surface area of a top cover material or bodyfacing surface of the article.

Figure 2A:
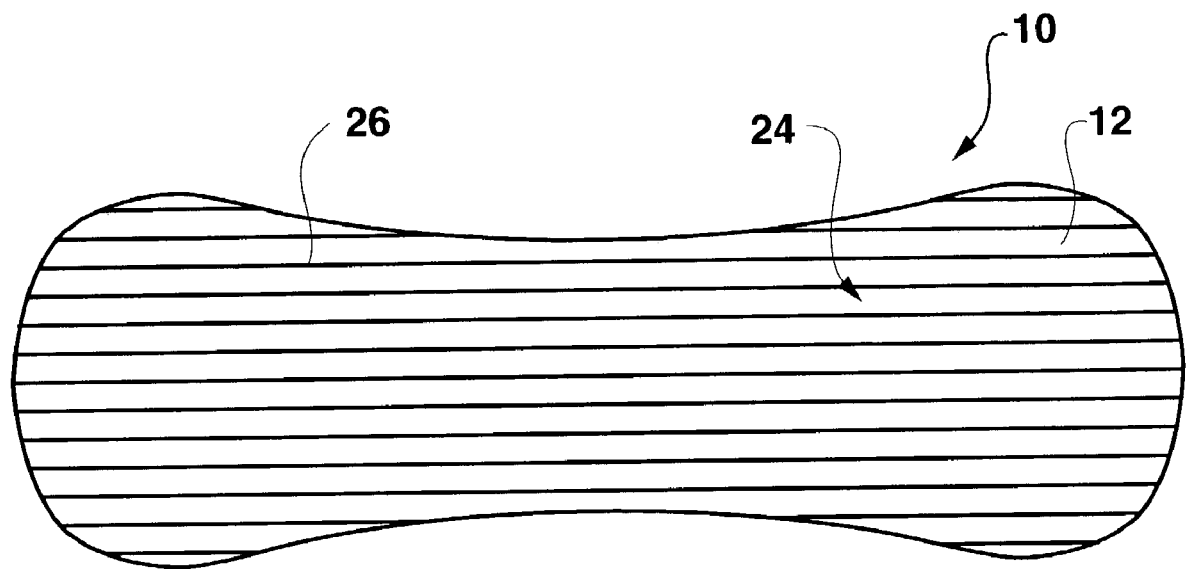
FIG. 2A is a top plan view of an embodiment of an absorbent article according to the invention.
Figure 2B:
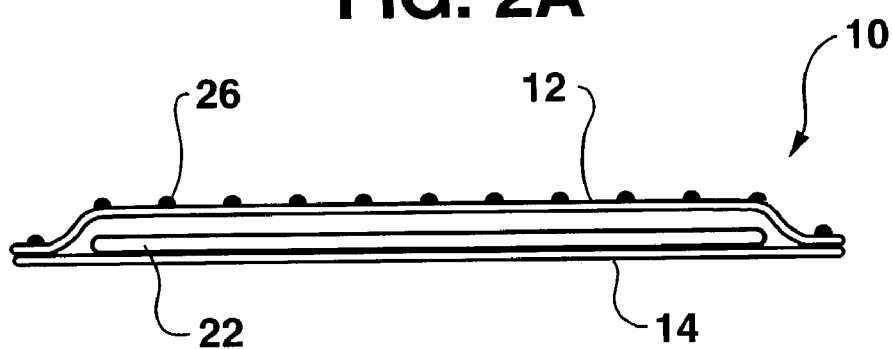
FIG. 2B is a cross-sectional view of an embodiment of an absorbent article according to the invention.
Figure 2C:
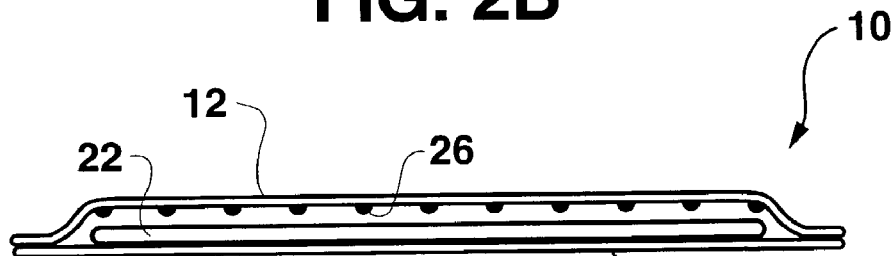
FIG. 2C is a cross-sectional view of an embodiment of an absorbent article according to the invention.
Figure 2D:
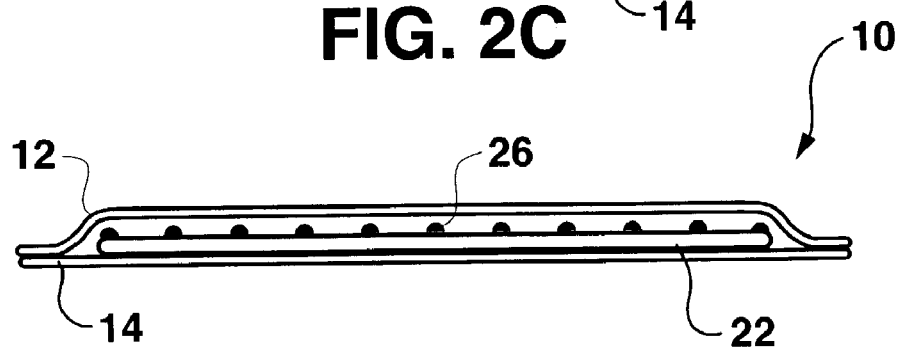
FIG. 2D is a cross-sectional view of an embodiment of an absorbent article according to the invention.

FIG. 2A is a bodyfacing view of an absorbent article 10 incorporating a distinct and highly visible pattern 24 of an odor control agent 26. In this example, the pattern 24 is defined by parallel stripes visible over generally the entire surface area of the top cover 12. As discussed above, the pattern 24 may take on any desired configuration, such as a wave pattern, floral pattern, etc. Referring to FIG. 2B, the pattern 24 may be defined on the bodyfacing surface of the top cover material 12. In an alternate embodiment as illustrated in FIG. 2C, the pattern may be defined on the underlying surface of the top cover 12 and still be highly visible from the body-facing side of the article 10. In alternate embodiments, the pattern may be defined on any of the underlying materials, such as the intake member 18, transfer delay member 20. In the embodiment of FIG. 2D, the agent 26 may be applied directly onto the absorbent material 22 in the absence of an intake layer or transfer delay member. If applied to an underlying material layer, the top cover member 12 is generally opaque or "see-through" so that the pattern 24 is readily visible though the material 12.

As mentioned, as a measure of the relative degree of visibility of the pattern 24 against its respective background, a gray-level difference value may be determined. In a particular embodiment, the contrast may have a gray level value of about 45 on a scale of 0 to about 255, where 0 represents "black" and 255 represents "white." The analysis method may be made with a Quantimet 600 Image Analysis System (Leica, Inc., Cambridge, UK). This system's software (QWIN Version 1.06A) enables a program to be used in the Quantimet User Interactive Programming System (QUIPS) to make the gray-level determinations. A control or "blank" white-level was set using undeveloped Polaroid photographic film. An 8-bit gray-level scale was used (0-255) and the program allowed the light level to be set by using the photographic film as the standard. A pad cover region was then measured for its gray-level value, and this was followed by the same measurement being made on an odor control agent region. The routine was programmed to calculate the gray-level value of the odor control agent region automatically. The difference in gray-level value between the agent and its respective background may be about 45 or greater in a particular embodiment for a desired level of contrast between the agent and its background.

The invention is not limited to any particular type of odor control agent 26 or application method. The agent 26 may be, for example, activated carbon, colored activated carbon, a colored odor absorbent such as zeolite, chitin, ion exchange resins, and so forth. The agent may be dark colored, such as activated carbon, or light colored, such as zeolite or silica. In a particular embodiment, the agent 26 may be in particulate form, such as a molecular sieve material (generally in the size range of 1-5 um). The particulate agent 26 may be applied to the article material in the form of an aqueous slurry containing the particulate agent 26, a binding agent, a wetting agent, and so forth. Illustrative binding agents include polyvinyl alcohol, methyl cellulose, carboxy methyl cellulose, starch (including ethylated and oxidized derivatives thereof), and various polymer emulsions. The slurry may be applied in the desired pattern 24 by various techniques, such as print (including screen printing), spraying, contact coated, blade, saturant, coating, droplet throw, paint, and foam applications.

In an alternate embodiment, an adhesive or binding agent may be applied in a desired pattern onto a substrate with subsequent application of a particulate odor control agent over the patterned adhesive. Alternately, the adhesive or binding agent may be applied generally uniformly over the material, and the particulate agent may be applied in a desired pattern to an adhesive coated substrate material.

EP 0 392 528 A2 describes methods of applying a slurry containing a particulate odor control agent to a web material of an absorbent article, such methods and slurries being useful for practice of embodiments according to the present invention. The EP 0 392 528 A2 reference is incorporated herein by reference for all purposes.

Activated carbon is a particularly desirable odor control agent for use with the present invention due to its black color. Carbon in particulate form may be applied in the desired pattern 24 using conventional methods as described above. In an alternate embodiment, the carbon agent is activated carbon applied as a coating in the desired pattern. The coating may include a polymeric material and an activation agent and, after application in the desired pattern, the substrate is heated to a temperature sufficient to induce carbon activation.

A variety of techniques may be utilized to apply the coating of the polymeric material and the activation agent to the fibers. For instance, in one embodiment, a polymeric material is initially dissolved in a solvent, mixed with a chemical activation agent, and then applied to the fibers. Alternatively, the chemical activation agent may initially be applied to the fibers. Thereafter, the polymeric material may be applied to the fibers. Moreover, the polymeric material may also initially be applied to the fibers prior to application of the chemical activation agent.

When the polymeric material and/or chemical activation agent are applied to a formed fibrous substrate, for instance, any known method of application may be utilized, such as print, spraying, contact coated, blade, saturant, coating, droplet throw, paint, and foam applications. For instance, in one particular embodiment, the polymeric material, the chemical activation agent, or a mixture thereof is applied to the fibrous substrate in the desired pattern (e.g., reticular pattern, diamond-shaped grid, dots, stripes, and the like). Moreover, in another embodiment, the polymeric material, the chemical activation agent, or a mixture thereof can be printed onto at least one side of the fibrous substrate, and, in some cases to both outer surfaces of the substrate.

The add-on level of the activated carbon coating to the fibrous substrate may generally be varied as desired. The "add-on level" refers to the mass of the activated carbon coating divided by the oven-dry mass of the uncoated substrate, multiplied by 100%. For example, a 5-gram non-woven web with 5 grams of added activated carbon would have an add-on of 100%. The add-on level can be expressed in terms of total activated carbon relative to total substrate weight, or, in the case of heterogeneously treated substrates, the "local" add-on value can be expressed in terms of the mass of the activated carbon in a particular region coated with activated carbon relative to the mass of the fraction of the substrate that for which at least one surface has been provided with the activated carbon coating. Generally speaking, a lower add-on level results in a lower increase in substrate stiffness, while a higher add-on level results in the presence of a greater amount of activated carbon on the substrate. Thus, in some embodiments, the activated carbon can have an add-on level of from about 1% to about 300% of the mass of the substrate, in some embodiments from about 5% to about 200% of the mass of the substrate, in some embodiments from about 5% to about 100% of the mass of the substrate, and in some embodiments, from about 5% to about 50% of the mass of the substrate.

The resulting activated carbon fibrous substrate is capable of performing multiple functions when incorporated into an absorbent article. For example, an absorbent nonwoven substrate may continue to function in its absorbent capacity within the article, but also have additional functions stemming from the presence of activated carbon therein, such as adsorbing odor-producing materials.

The surface chemistry of the activated carbon coating may be tailored to optimize odor reduction or other additional functions performed by the fibrous substrate. For example, basic groups are desired on the activated carbon fibers for adsorbing acidic compounds, such as isovaleric acid or hydrochloric acid. Basic groups can be introduced by treatment with ammonia at elevated temperatures or by other treatments known in the art. In one embodiment, to form a basic surface chemistry, nitrogen containing polymeric materials may be used, such as polyacrylonitrile (PAN), with an activation agent (e.g., zinc chloride). In one particular embodiment, this coating mixture is heated to about 300° C. to about 400° C. for about 2 minutes to about 24 hours. The resulting assemblies have B.E.T. surface areas of about 400 and 1200 $m^2/g$ and a nitrogen content ranging from about 12 wt. % to about 20 wt. % based upon the weight percent of activated carbon coating. Optionally, much higher temperatures, e.g., up to about 900° C., may be used for increased surface areas.

In addition, acidic groups are desired on the activated carbon fibers for adsorbing basic compounds, such as those having ammonium moieties. Acidic groups can be introduced by treating the fibers at elevated temperatures in the presence of steam, carbon dioxide, nitric acid, and the like. In one embodiment, oxygen containing polymeric materials, such as polyvinyl alcohol (PVA) or cellulose, may be used with an activation agent (e.g., phosphoric acid). In one particular embodiment, such a coating mixture is heated to from about 150° C. to about 300° C. for about 2 minutes to about 24 hours.

To maintain absorbency, flexibility, or some other characteristic of the fibrous substrate, it may be desired to apply the polymeric material, the chemical activation agent, or a mixture thereof in the desired pattern so as to cover less than about 100% of the surface area of the substrate, in some embodiments from about 10% to about 80% of the surface area of the substrate, and in some embodiments, from about 20% to about 60% of the surface area of each side of the fibrous substrate. Such a patterned coating may provide sufficient activation to the fibrous substrate without covering a substantial portion of the surface area of the substrate. This may be desirable to optimize flexibility, absorbency, or other characteristics of the resulting absorbent article.

The polymeric material of the coating may be any organic polymer that will react with a chemical activation agent to produce an activated carbon coating. Examples of suitable polymeric materials that may be used include, but are not limited to, phenolic resins, poly(vinyl alcohol) (PVA), polyacrylonitrile (PAN), cellulose or other natural or synthetic polysaccharides, cellulose derivatives or other polysaccharide derivatives, polystyrene, polypropylene, poly(vinyl chloride) (PVC), poly(meth)acrylates and poly(meth)acrylic acids, polylactic acid, and combinations thereof. Desirably, the polymeric material is soluble in a solvent. Examples of some suitable solvents include, but are not limited to, water; alcohols, such as ethanol or methanol; dimethylformamide (DMF); dimethyl sulfoxide; hydrocarbons, such as pentane, butane, heptane, hexane, toluene and xylene; ethers, such as diethyl ether and tetrahydrofuran; ketones and aldehydes, such as acetone and methyl ethyl ketone; acids, such as acetic acid and formic acid; amines, such as pyridine and hexamethylenetetramine; and halogenated solvents, such as dichloromethane and carbon tetrachloride; and the like.

As stated, the activation agent reacts with the polymeric material to form the activated carbon coating at an elevated temperature. Although not required, Lewis acids and bases may be employed as the activation agents in the present invention. Some examples of such activation agents are described in U.S. Pat. No. 5,834,114 to Economy, et al.; WO 01/97972 to Economy, et al.; and U.S. Patent Publication No. 2001/0024716, which are incorporated herein in their entirety by reference thereto for all purposes. Specific examples include, but are not limited to, acids, such as phosphoric acid; metal halides, such as zinc chloride; and hydroxides, such as potassium hydroxide and sodium hydroxide. Other examples include Friedel-Crafts compounds; dehydrating agents; TiC$_4$, ZnBr$_2$, AlBr$_3$, AlCl$_3$, BF$_3$, CaO, Ca(OH)$_2$, H$_2$SO$_4$, Mg(OH)$_2$, MgO and LiOH.

The amount of the activation agent within the mixture may generally vary as desired. For example, in some embodiments, the activation agent is present in the coating mixture in an amount of from about 0.1 wt. % to about 90 wt %. As the amount of activation agent is increased, the pore size of the resulting activated carbon coating also increases. After reaction has occurred, some or all of the remaining activation agent can be washed out of the activated carbon coating, if desired. For example, substantially all of the remaining activation agent can be removed by washing with water or other substances, or a lesser portion of the remaining activation agent can be removed, such as from about 1% to about 99%, from about 10% to about 99%, or from about 20% to about 99%, or from about 50% to about 95%, or from about 60% to about 95% of the remaining activation agent. In some embodiments, a portion of the activation agent (e.g., a zinc salt or an acidic compound like phosphoric acid or its salts) is left to serve additional functions, such as ion exchange, antimicrobial functions, removal of target species by chemical reaction or neutralization, pH control, viscosity control, surface tension modification, and the like. In such embodiments, the percentage of the initial activation agent or its soluble reaction products that is retained in the activated carbon fabric can be at least about 10%, more specifically at least about 20%, and most specifically at least about 30%.

The activated carbon coating may include one or more catalytic materials that remain inert during processing but catalyze the decomposition of byproduct gases. Examples of suitable catalysts include, but are not limited to, free metal or compounds of metals, such as zinc, copper, platinum, palladium and titanium. In some embodiments, the metal is present as the free metal or the oxide (such as zinc oxide, titanium dioxide, or copper oxide). The catalyst may be applied by mixing it or a compound of the metal of the catalyst into the coating mixture, or after activation by coating the activated carbon coating with a mixture of catalyst, or a compound containing the metal of the catalyst, and a solvent, and then vaporizing the solvent. For example, the metal of the catalyst may be applied as the chloride salt with a solvent, and then heated to remove the solvent and convert the chloride salt to an oxide or the free metal. Any volatile solvent capable of dispersing or dissolving the catalyst or a compound of the metal of the catalyst is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof.

Once the mixture is formed, it is then heated to crosslink the polymeric material. Generally, the entire substrate or the entire coated portion of the substrate is heated to activate the coating, though a portion (e.g., less than 50%) of the substrate may be kept at a lower temperature than the remaining fabric if desired. The elevated temperature is generally maintained sufficiently long to at least partially activate the coating (e.g., from about 30 seconds to about 30 minutes). In some embodiments, heating is carried out at a temperature of from about 100° C. to about 250° C., in some embodiments from about 170° C. to about 250° C., and in some embodiments, from about 170° C. to about 200° C. The use of such low curing temperatures allows, in some embodiments, the resulting substrate to have an activated carbon coating without substantially sacrificing the flexibility or other mechanical properties of the substrate. Further, such low curing temperatures also allow for the use of polymers having low softening or decomposition temperatures (e.g., polyester) that are commonly employed in absorbent articles. In addition, not only does heating crosslink and activate the polymeric material, it also forms a durable coating that will generally remain present on the fibers during use. In one embodiment, the activated carbon coating on the fibrous substrate does not rub off to a significant degree when the coating is rubbed between the fingers of the human hand.

If desired, activation may take place in one or more incremental steps over a succession of temperatures to increase the concentration of porosity in the coating and minimize the amount of coating that is volatilized. Optionally, the cured coating may be further activated to produce a higher surface area by further heating in the presence of an inert gas or air. Selection of the specific polymeric material, chemical activation agent and its concentration, along with the activation temperature and time, will determine the specific surface area, pore size distribution and surface chemistry of the activated carbon coating. For example, low activation temperatures can be used to produce high surface area activated carbon coating fibers.

The characteristics of the resulting activated carbon coating generally vary based on the amount and type of the polymeric material and activation agent utilized. For example, in some embodiments, the amount of carbon in the coating is less than about 85 wt %, in some embodiments less than about 80 wt %, in some embodiments, from about 50 wt % to about 80 wt %, and in some embodiments, from about 60 wt. % to about 75 wt % of the fibers. In addition, the yield of activated carbon in the coating (the weight of activated carbon coating divided by the weight of coating mixture) may be at least about 50%, in some embodiments at least about 60%, in some embodiments at least about 80%, and in some embodiments, at least about 90%. Further, the resulting coating may have a B.E.T. surface area (measured using a "Quantachrome Autsorb-1" available from Quantachrome Instruments, Inc. of Boynton Beach, Fla.) of at least about 50 m$^2$/g and an average pore size of from about 5 Angstroms (Å) to about 35 Å. Prior to heating, the coating mixture may have a surface area of up to about 10 m$^2$/g.

The solutions to be coated onto a substrate can have a viscosity of at least about 1 centipoise (cp), in some embodiments at least about 5 cp, in some embodiments at least about 10 cp, and in some embodiments, at least about 50 cp. If desired, thickeners and/or surfactants can be used to apply the coating material to the polymeric substrate. In one embodiment, the coating can be prepared as a foam that can collapse during heat treatment to increase the basis weight of the applied coating. Foams can be prepared by agitation of the solution in the presence of a surfactant. Thickeners, such as sodium alginate, xanthan gum, gum arabic, guar gum, sodium alginate, polyvinyl alcohol, bentonite, laponite, kaolin, and the like, may be used in the present invention.

The odor control agent 26 (either in slurry form or activated carbon coating form) may be applied to a material used in the article 10 in the desired pattern 24 by conventional printing techniques, such as a piezo-driven print head. The piezo-driven print devices are typically capable of emitting droplets having a diameter in the range of about 50-90 micrometers with placement resolution to about ¹⁄₂₀₀ of an inch. The odor control agent composition may be deposited in a single or multiple pass of the material past the print head. In an alternate desirable embodiment, the composition may be deposited by an inkjet printing technique. Suitable inkjet printing techniques are described, for example, in co-pending U.S. patent application Ser. No. 09/990,686 filed on Nov. 16, 2001, and entitled "MATERIAL HAVING ONE OR MORE CHEMISTRIES WHICH PRODUCE TOPOGRAPHY, UNIQUE FLUID HANDLING PROPERTIES AND/OR BONDING PROPERTIES THEREON AND/OR THEREIN" and U.S. patent application Ser. No. 09/991,185 filed on Nov. 16, 2001, and entitled "APPARATUS AND METHOD TO PRODUCE TOPOGRAPHY, UNIQUE FLUID HANDLING PROPERTIES AND BONDING PROPERTIES ON OR WITHIN SUBSTRATES." These co-pending applications are incorporated herein by reference for all purposes.

Figure 3:
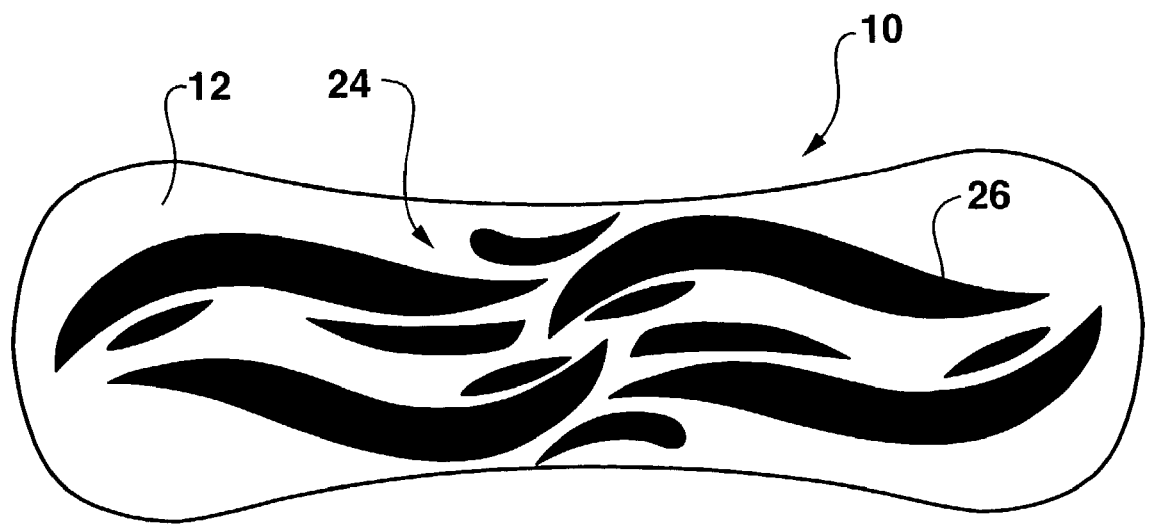
FIG. 3 is a top plan view of an alternate embodiment of an absorbent article according to the invention.

FIG. 3 illustrates an embodiment of an article 10 wherein the pattern 24 of odor control agent is defined as a highly visible flowing abstract design using variously shaped curves. It should be appreciated that virtually any conceivable artistic or abstract design may be used. The design may encompass all or less than all of the visible surface area of the bodyfacing side of the article 10.

In FIG. 3, the abstract curved shapes are defined by sharp, crisp lines so that the contrast between the shapes and background is quite distinct. This concept may be used for any design pattern. In alternate embodiments, however, it may be desired that the lines of demarcation are far less crisp. For example, for a unique appearance, it may be desired that the design shapes have a "fuzzy" or blurred outline so that they merge gradually with the background.

Figure 4:
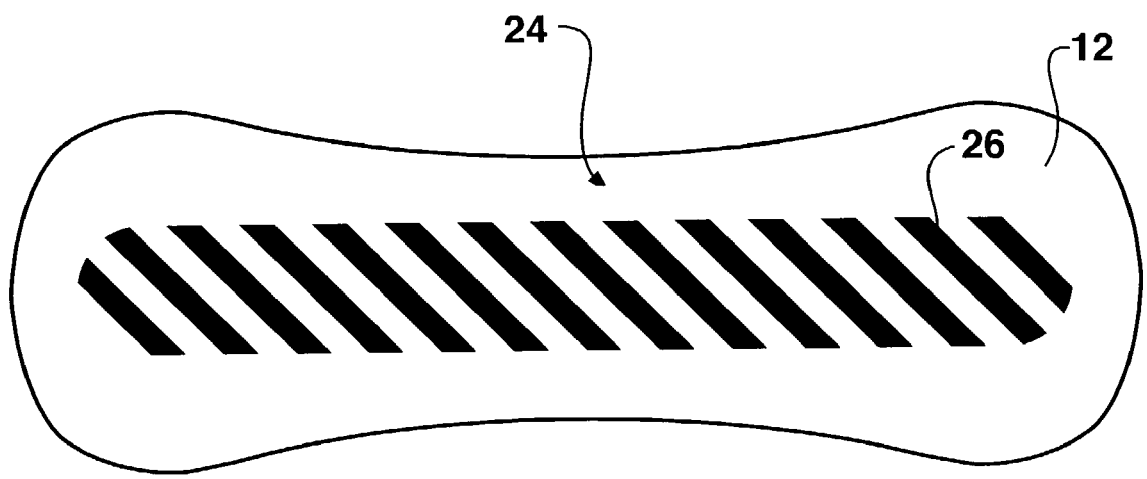
FIG. 4 is a top plan view of an alternate embodiment of the invention.

FIG. 4 illustrates an embodiment of an article 10 wherein the pattern 24 is defined by oblique parallel stripes focused in a central longitudinally extending region of the article 10. For many products, this central area constitutes an "insult" area that receives bodily exudates. In situations wherein staining of the insult area is potentially embarrassing for consumers, it may be desired to focus the pattern 24 in the insult area so as to disguise or mask any staining.

Figure 5:
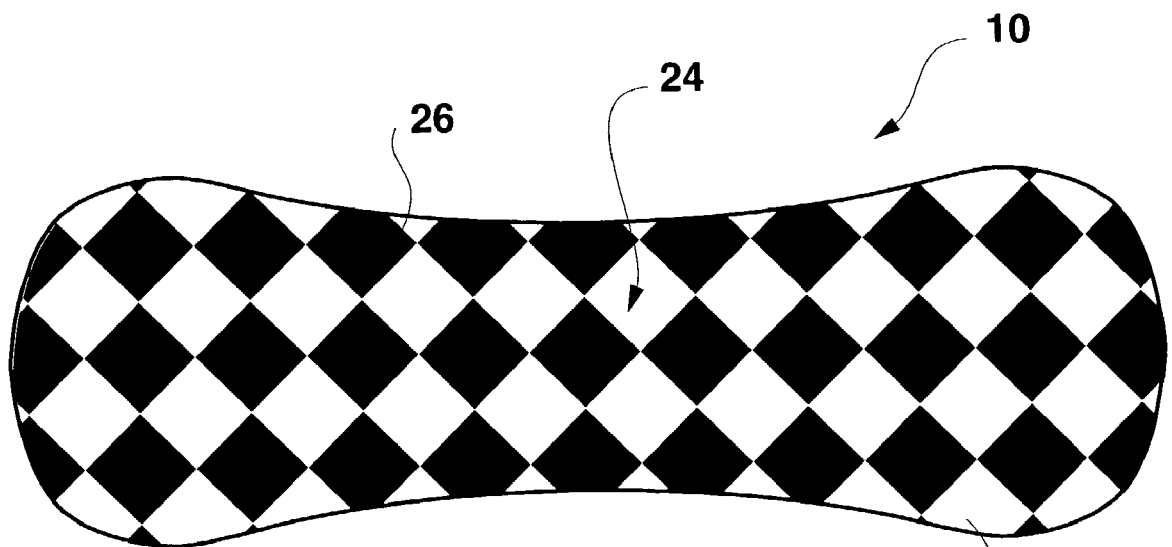
FIG. 5 is a top plan view of an alternate embodiment of the invention.

FIG. 5 illustrates an alternate embodiment wherein the pattern is defined by an overall diamond shape pattern 24 of the odor control agent 26. It should be appreciated that any pattern of geometric shapes is within the scope and spirit of the invention.

Figure 6:
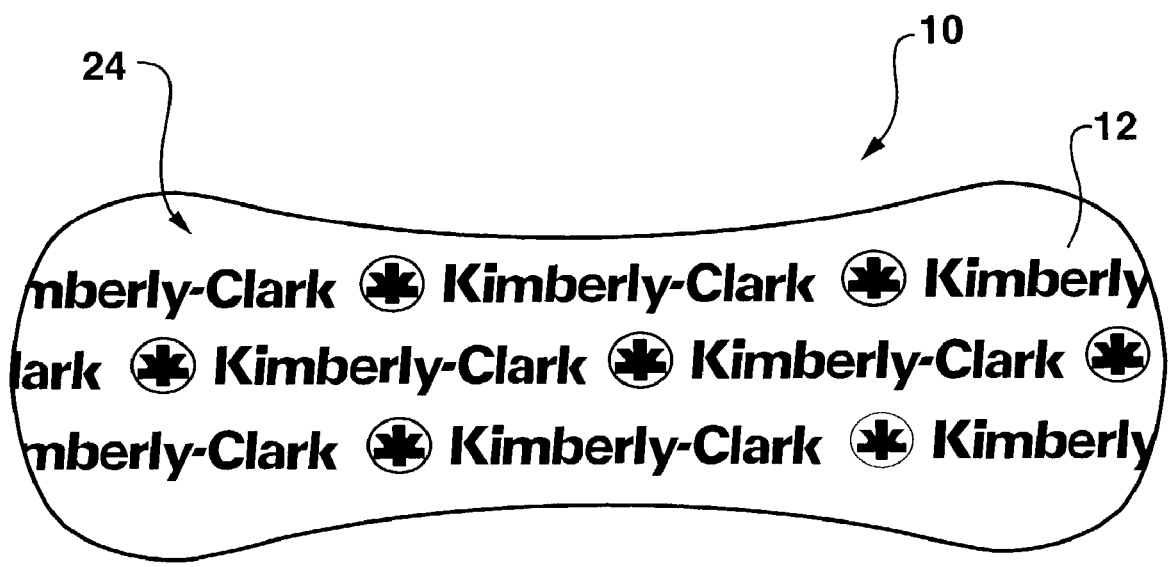
FIG. 6 is a top plan view of an alternate embodiment of the invention.

FIG. 6 illustrates an embodiment wherein the pattern 24 of odor control agent is defined by printed indicia. In the illustrated embodiment, the indicia is a trademark symbol and logo of the manufacturer. It should be appreciated that any manner of indicia may be used in this regard.

Figure 7:
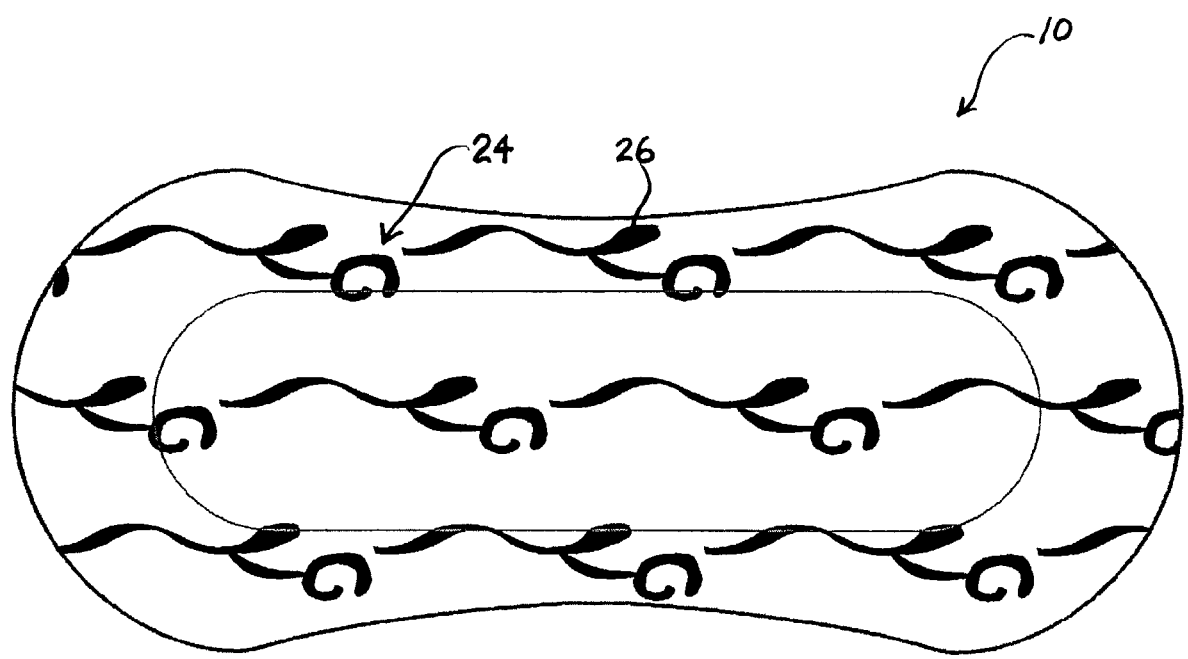
FIG. 7 is a top plan view of an alternate embodiment of the invention.

FIG. 7 illustrates a floral pattern 24 of odor control agent 26.

It should be appreciated by those skilled in the art that various modifications and variations can be made to the embodiments of the absorbent article described herein without departing from the scope and spirit of the invention as set forth in the appended claims and equivalents thereof.

What is claimed is:

1. An absorbent article, comprising a top cover and a material layer disposed beneath said top cover, an odor control agent deposited in a visible pattern between said top cover and said material layer of said article, which material layer is separated from contacting said top cover in regions where said visible pattern of odor control agent is deposited, said odor control agent comprising a color so as to present a distinguishable pattern against a contrasting colored background defined by said material layer, and wherein said top cover defining a bodyfacing surface of said absorbent article, said distinguishable pattern of odor control agent disposed visibly beneath said top cover and discernible to the user when viewed through said bodyfacing surface.

2. The absorbent article as in claim 1, wherein said article comprises a feminine care absorbent article.

3. The absorbent article as in claim 2, wherein said article is a sanitary napkin.

4. The absorbent article as in claim 1, wherein said odor control agent comprises carbon.

5. The absorbent article as in claim 4, wherein said carbon comprises particulate carbon particles attached to said material layer in said pattern.

6. The absorbent article as in claim 4, wherein said carbon comprises an activated carbon coating applied to said material layer in said pattern.

7. The absorbent article as in claim 1, wherein the contrast between said odor control agent and said contrasting background has a minimum gray scale value of at least about 45 on a scale of 0-255.

8. The absorbent article as in claim 1, wherein said pattern of odor control agent is defined in selected regions of said bodyfacing surface.

9. The absorbent article as in claim 8, wherein said article is a feminine care hygiene article, said pattern of odor control agent defined in a central insult region of said bodyfacing region.

10. The absorbent article as in claim 8, wherein said article is a feminine care hygiene article, said pattern of odor control agent defined around a periphery of said bodyfacing region.

11. An absorbent article, comprising:
a liquid permeable top cover at a bodyfacing side of said article;
a generally liquid impermeable outer cover;
an absorbent structure disposed between said top cover and said outer cover;
an odor control agent disposed between said top cover and said absorbent structure in a pattern that is visible through said top cover, said odor control agent having a color that contrasts with a color of said bodyfacing side of said article such that a minimum contrast gray scale value of at least about 45 on a scale of 0-255 is defined between said odor control agent and said bodyfacing side; and
wherein said odor control agent is deposited in said pattern on an inner surface of said top cover and is distinguishable through said top cover from said bodyfacing side of said article against a contrasting colored background defined by an upper surface of said absorbent structure.

12. An absorbent article, comprising:
a liquid permeable top cover at a bodyfacing side of said article;
a generally liquid impermeable outer cover;
an absorbent structure disposed between said top cover and said outer cover;
an odor control agent disposed in a pattern that is visible from said bodyfacing side of said article, said odor control agent having a color that contrasts with a color of said bodyfacing side of said article such that a minimum contrast gray scale value of at least about 45 on a scale of 0-255 is defined between said odor control agent and said bodyfacing side; and
wherein said pattern of odor control agent is defined on a material layer of said absorbent structure and is visible through said top cover without substantial alteration of said pattern by said top cover, said pattern of odor control agent distinguishable against a contrasting colored background defined by an upper surface of said material layer.

13. An absorbent article, comprising a top cover defining a bodyfacing surface of said absorbent article and a material layer disposed beneath said top cover, an odor control agent deposited in a visible pattern between said top cover and said material layer of said article, said odor control agent comprising a color so as to present a distinguishable pattern against a contrasting colored background defined by said material layer, said distinguishable pattern of odor control agent and contrasting colored background disposed visibly beneath said top cover and discernible to the user through said top cover when viewed through said bodyfacing surface.

14. The absorbent article as in claim 13, wherein said pattern of odor control agent encompasses between about 10% to about 75% of a surface area of said top cover.

15. The absorbent article as in claim 13, wherein said pattern of odor control agent comprises a pattern of parallel stripes.

16. The absorbent article as in claim 13, wherein said article comprises a feminine care absorbent article.

* * * * *

UNITED STATES PATENT AND TRADEMARK OFFICE
CERTIFICATE OF CORRECTION

PATENT NO. : 7,626,072 B2 Page 1 of 1
APPLICATION NO. : 10/328338
DATED : December 1, 2009
INVENTOR(S) : Cheryl A. Mocadlo It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 442 days.

Signed and Sealed this

Second Day of November, 2010

David J. Kappos
*Director of the United States Patent and Trademark Office*